(12) United States Patent
Heide et al.

(10) Patent No.: US 7,012,034 B2
(45) Date of Patent: Mar. 14, 2006

(54) RESORBABLE BONE REPLACEMENT AND BONE FORMATION MATERIAL

(75) Inventors: Helmut Heide, Kelkheim (DE); Joachim Pabst, Reinheim (DE); Albrecht Dinkelaker, Morfelden-Walldorf (DE); Olaf Pobantz, Wiesbaden (DE)

(73) Assignee: curasan AG, Kleinostheim (DE)

( * ) Notice: Subject to any disclaimer, the term of this patent is extended or adjusted under 35 U.S.C. 154(b) by 0 days.

(21) Appl. No.: 10/930,965

(22) Filed: Aug. 31, 2004

(65) Prior Publication Data

US 2005/0027367 A1 Feb. 3, 2005

Related U.S. Application Data

(63) Continuation of application No. 10/085,526, filed on Feb. 26, 2002, which is a continuation-in-part of application No. PCT/EP00/08382, filed on Aug. 28, 2000.

(30) Foreign Application Priority Data

Aug. 26, 1999 (DE) ................................ 199 40 717

(51) Int. Cl.
  *C04B 35/447* (2006.01)
  *A61F 2/28* (2006.01)
(52) U.S. Cl. ........................ 501/1; 623/23.5; 623/23.56
(58) Field of Classification Search .................. 501/1, 501/80; 623/23.5, 23.56
See application file for complete search history.

(56) References Cited

U.S. PATENT DOCUMENTS

| 4,195,366 | A | | 4/1980 | Salsbury et al. |
| 5,096,814 | A | * | 3/1992 | Aivasidis et al. ............... 435/41 |
| 5,141,510 | A | * | 8/1992 | Takagi et al. ............ 301/111.06 |
| 5,531,794 | A | * | 7/1996 | Takagi et al. ............. 623/23.56 |
| 6,340,648 | B1 | * | 1/2002 | Imura et al. ..................... 501/80 |
| 6,383,519 | B1 | | 5/2002 | Sapieszko et al. |
| 6,511,510 | B1 | * | 1/2003 | de Bruijn et al. ......... 623/23.56 |
| 6,521,246 | B1 | | 2/2003 | Sapieszko et al. |
| 6,905,516 | B1 | * | 6/2005 | Lemaitre et al. ......... 623/23.56 |
| 2004/0019385 | A1 | * | 1/2004 | Ayers et al. ................. 623/23.5 |
| 2004/0064194 | A1 | * | 4/2004 | Irie et al. .................. 623/23.61 |

FOREIGN PATENT DOCUMENTS

| DE | 3123460 A | 2/1982 |
| DE | 3810803 A | 10/1989 |
| DE | 29922585 | * 7/2000 |
| JP | 1-108143 | 4/1989 |

OTHER PUBLICATIONS

DE 3810803, Derwent Abstract, Oct. 12, 1989.*
DeGroot et al., *Die klinische anwendbarkeit von Calciumphosphat-Keramiken*, Zahnarztliche Mitteilungen Heft 18/85, 75. Jahrgrang (1985, pp. 1938-1940.
Roempp Chemie-Lexikon ed. 7 (1975, Franckhsche Veriagsbuchhaltung Stuttgart.
Koster, K. Heide H. Konig R., Histologische Untersuchungen an der Grenzflache zwischen Knochengewebe und Calciumphosphat-, Calciumaluminat- und Aluminiumoxidkeramik, Z. Orthop. 115 (1977), pp. 693-699.

(Continued)

*Primary Examiner*—Karl Group
(74) *Attorney, Agent, or Firm*—Myers Bigel Sibley & Sajovec PA

(57) ABSTRACT

The invention relates to a resorbable bone replacement and bone formation material (augmentation material) based on porous β-tricalcium phosphate (β-TCP).

85 Claims, 6 Drawing Sheets

OTHER PUBLICATIONS

DeGroot, Ph.D., Klaas (Editor); "Bioceramics of Calcium Phosphate", *CRC Press, Inc.*, Boca Raton, Florida (1983).

Meachim, G., Brooke G. and Pedley, R.B.; "The tissue response to acrylic particles implanted in animal muscle"; *Biomaterials* 1982, vol. 3 Oct.; pp. 213-219.

Sjoholm, Ingvar and Edman, Peter; "Acrylic Microspheres in Vivo. I. Distribution and Elimination of Polyacrylamide Microparticles after Intravenous and Intraperitoneal Injection in Mouse and Rat", *The Journal of Pharmacology and Experimental Therapeutics*, vol. 211, No. 3 (1979), pp. 656-662.

DeGroot, Dr. K;"Dieklinische Anwendbarkeit von Calciumphosphat-Keramiken", *Zahnarziliche Mittellungen Heft* 18/85—75 Jahrgang (1985), pp. 1938-1940.

Rompp Chemie Lexikon, ed. 7 (1975), Franckh'sche Verlagshandlung, Stuttgart.

Koster, K., Heide, H., Konig, R.; "Histologische Untersuchungen an der Grenzflache zwischen Knochengewebe und Calciumphosphat-, Calciumaluminat- und Aluminiumoxidkeramik", *Z Orthop.* 115 (1977), pp. 693-699.

Klawitter, J.J., Bagwell, J.G., Weinstein, A.M., Sauer, B.W.; "An Evaluation of Bone Growth into Porous High Density Polyethylene", *J. Biomed. Mater. Res.*, vol. 10 (1976), pp. 311-323.

510(k) *Summary* (Nov. 26, 2002) 2 pages.

510(k) *Summary Vitoss ™ Scaffold Synthetic Cancellous Bone Void Filler*, Summary of S&E, Vitoss Scaffold, Orthovita, Inc. (Dec. 14, 2000) pp. H1-H3.

Erbe et al., *Comparison of Vitoss and Pro Osteon 500R in a Canine Model at 1 Year*, 47th Annual Meeting, Orthopaedic Research Society (Feb. 26-28, 2001), p. 0975.

*Filling of Bone Defects with Tricalcium Phosphate Beta in Traumatology*, In Ann Chir Dec. 2000; 125(10):972-81 (concise statement).

Galols et al., *Use of β-tricalcium phosphate in foot and ankle surgery; a report of 20 cases*, Blackwell Science Ltd., Foot and Ankle Surgery Dec. 2001 7:217-227.

Indications for Use Statement, *Vitoss ™ Scaffold Synthetic Cancellous Bone Void Fitter*, Vitoss Scaffold 510(k) Notification (Dec. 7, 2000) 1 page.

Letter from Dept. of Health & Human Services re: *Synthes chronOS Tricalcium Phosphate and Synthes Perfusion Syringe* (Nov. 26, 2002), 2 pages.

Letter from Dept. of Health & Human Services re: *Vitoss™ Scaffold Synthetic Cancellous Bone Void Fitter* (Dec. 14, 2000), 2 pages.

\* cited by examiner a)

b)

c)

d)

e)

a)

b)

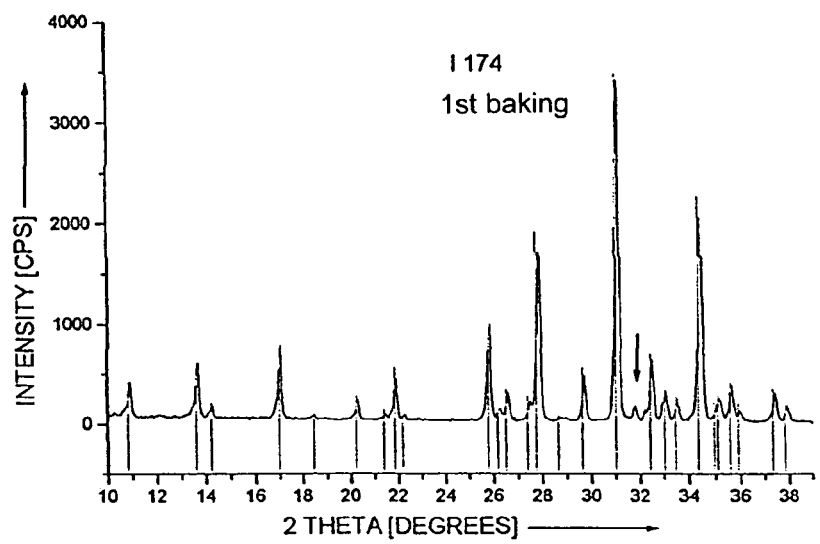

Fig. 4a Batch I 174 after the first synthesis baking. A residual reflection of hydroxyapatite (arrow) is clearly discernible. The red lines denote β-TCP.

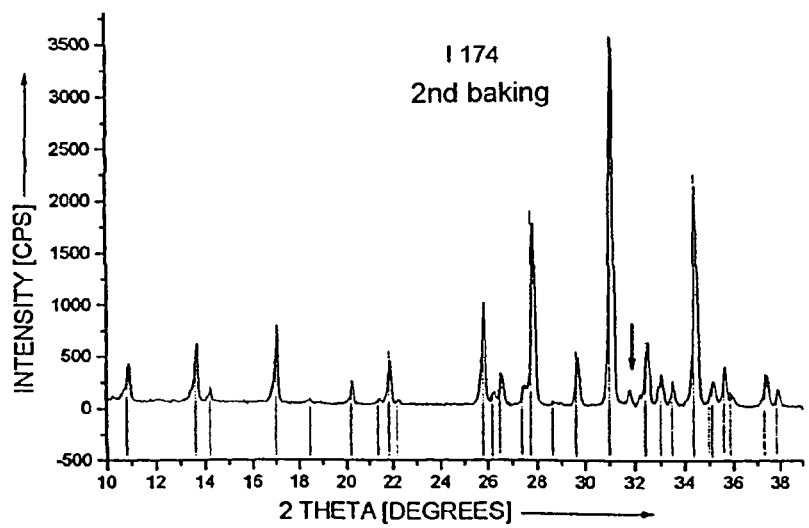

Fig. 4b X-ray powder diffraction diagram of batch I 174 after grinding, compaction and repeat baking. Unreacted starting material was not added. The reflection of hydroxyapatite (arrow) has not changed in relation to the reflections of β-TCP.

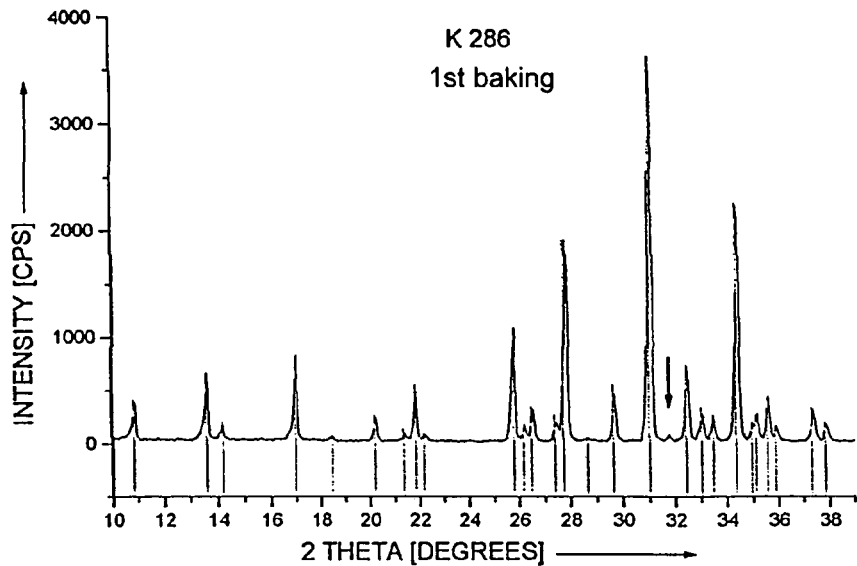
Fig. 5a Batch K 286 after the first synthesis baking. A hydroxyapatite reflection (arrow) is discernible.
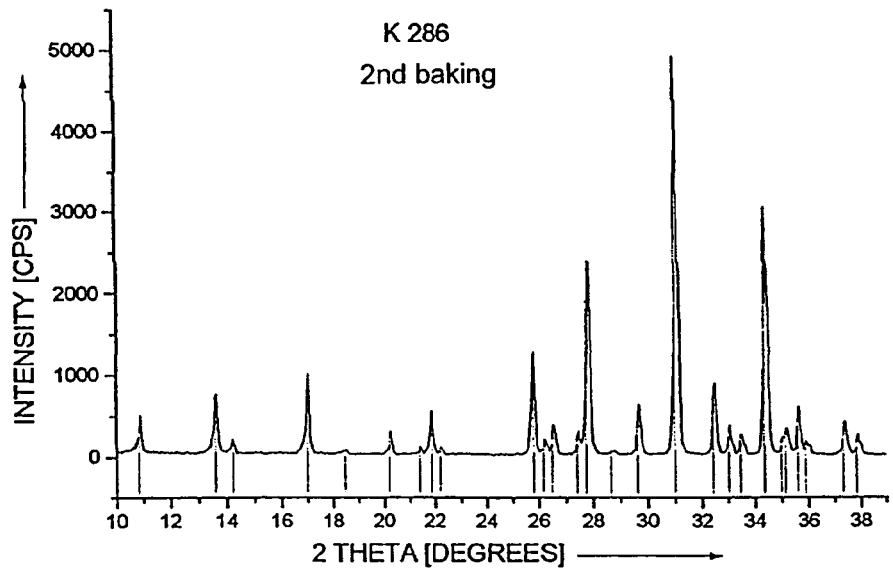
Fig. 5b Batch K 286 after comminution, addition of unreacted starting material and second synthesis baking. Hydroxyapatite is no longer discernible.

RESORBABLE BONE REPLACEMENT AND BONE FORMATION MATERIAL

RELATED APPLICATIONS

This application is a continuation of U.S. patent application Ser. No. 10/085,526, filed on Feb. 26, 2002, which is a continuation-in-part of International PCT Application Serial No. PCT/EP00/08382 filed on Aug. 28, 2000, which claims the benefit of priority of DE 19940717.7, filed Aug. 26, 1999. The contents of the above documents are hereby incorporated by reference as if recited in full herein.

BACKGROUND a) Phase Purity

Since the sixties, calcium orthophosphates, especially α- and β-tricalcium phosphate (TCP) and also hydroxyapatite (HAP) have been investigated and used as so-called bioactive and resorbable bone replacement materials. A comprehensive materials science and biomedical literature exists on the subject, in which respect, by way of example, reference may here be made to the comprehensive summary by K. deGroot: Bioceramics of Calciumphosphates. K. deGroot (Editor) CRC Press, Boca Raton, Fla. 1983, 1. The good biocompatibility of that group of materials is understandable considering the extensive chemical similarity of those materials to the inorganic constituent of bone, hydroxyapatite. The scientific discoveries from the period of pioneering research into that group of materials are adequately described by the work referred to above. Accordingly, the good compatibility with bone, the more or less pronounced resorbability and the so-called "bioactivity" are reported, bioactivity being understood to mean the positive chemical interaction of those calcium phosphates with living bone, which finds expression in the formation of a direct bond, without connective tissue, with the bone. The precise links between the materials characteristics and the biological properties of those materials have not, as yet, been clarified in many regards and it is only in recent times that discoveries have been made in respect of the correlation between the materials science, thermodynamic and crystallographic characteristics of those materials and the biological reactions of bone.

In the case of foreign-body reactions of bone it is generally assumed that particles less than 20 micrometers in size are taken up and transported away or metabolized (phagocytosis) by macrophages (phagocytes). Those processes are discussed, inter alia, in the following publications: Meachim et al. in Biomaterials, 3 (4) (1982) 213–219 and Sioholm et al. in J. Pharmacol. Exp. Ther., 211 (3) (1979) 656–662.

In a further study, deGroot reports (DeGroot et al.: Die klinische Anwendbarkeit von Calciumphosphat Keramiken [The clinical applicability of calcium phosphate ceramics]. Z. M. Fortbildung 75, 1985, 1938–1940) on the particulate breakdown of TCP into phagocytosable sub-particles which can pass into the lymphatic system. According to findings on which the invention is based, those phenomena have something to do with the phase make-up, phase purity and structure of the TCP material investigated therein. Accordingly, the two most important forms of TCP, α- and β-TCP, despite their chemical similarity, have different solubilities and, especially, different conversion characteristics in the biological environment. In many TCP materials, the two forms of tricalcium phosphate are present together, with phases of lesser stability (lattice energy and solubility) being concentrated at the particle boundaries. When heterogeneous materials of that kind are subjected to continuing chemical dissolution and biological degradation processes, such a material will break down in the manner described by De Groot. Because of the concentration of "foreign phases" at the particle boundaries of the principal constituents of the material, that breakdown process mechanism is active even when there are very small amounts of phase impurities. From that it follows that such resorbable implant materials must be very carefully synthesised in phase-pure form. In the case of materials corresponding to the prior art, that requirement is clearly not met. (G. Bauer and G. Hohnberger: Ursachen unterschiedlichen Verhaltens von bioaktiven Calcium Phosphatkeramiken im Organismus [Causes of differing behaviour of bioactive calcium phosphate ceramics in the body]. cfi (Ber. d. DKG) 66 (1989), 23–27)

b) Porosity

Microporosity

Microporosity is understood to mean that porosity of a ceramic material which is no longer discernible to the naked eye, that is to say pore radii that are approximately $\leq 20$ micro-meters (Römpp Chemie Lexikon [Römpp Chemistry Dictionary], 7th Edition (1975), Franckh'sche Verlagshandlung, Stuttgart).

In addition to the phase purity, the nature of the pore structure of a resorbable bone replacement material is an important factor.

To begin with, it should first be stated that increasing the porosity of the structure increases the specific surface area and also, as a result, the resorbability. At the same time, the mechanical strength decreases and the tendency to particulate breakdown increases. In spite of that basic relationship, the prior art attempts to achieve a resorption rate that is as high as possible by providing the internal surface of the material with particle-to-particle binding that is as weak as possible by using or "cultivating!" constituents of the structure that are as finely particulate as possible. As expected, biomaterials according to the prior art that are "cultivated" for high resorption rates are mechanically so imperfect that they generally come into consideration only for applications in which no appreciable mechanical demands are made. The uncontrollable breakdown into microscopically fine sub-particles results, moreover, in increased formation of poly-nuclear giant cells, which has to be regarded as an unfavourable cellular reaction to the biomaterial in question. Rapid implant resorption occurring synchronously with restoration of newly formed bone, without the occurrence of any appreciable breakdown of the structure, is desirable.

According to the prior art, relatively large, formed, monolithic pieces made from such microporous materials are also used as implants for bridging relatively large bone defects. In the case of such formation materials, in which only microporous material structures are present, it is found that, after superficial resorption, pronounced stagnation of the resorption process takes place after a short time and, later, rejection processes may even occur. According to findings on which the invention is based, those phenomena are in no way to be attributed to the chemical material properties of the calcium phosphates in question but, rather, are based on the following negative effect: The microporosity of those materials actually has a capillary suction effect on fluids in the region surrounding the implant. As a result, those fluids are drawn into the interior of the implant materials, where they remain for relatively long periods while newly formed bone grows around the external regions of the implant. Bone structures and blood vessels are not able to penetrate into the internal regions and the diffusion distances are too large for a diffusive exchange of substances. Accordingly, in the interior of such "inaccessible" regions of monolithic implant materials, necrosis of the body fluids and cells previously drawn in by the capillary action may occur.

Macroporosity

According to Römpp Chemie Lexikon [Römpp Chemistry Dictionary], 7th Edition (1975), Franckh'sche Verlagshandlung, Stuttgart, macroporosity is understood to refer to pore radii $\geq 20$ micrometers.

From as early as the seventies the possibility has been investigated of using calcium phosphate implant materials which have an open, interconnected macroporosity (K. Köster, H. Heide and R. König: Histologische Untersuchungen an der Grenzfläche zwischen Knochengewebe und Calciumphosphatkeramik etc. [Histological investigations at the boundary surface between bone tissue and calcium phosphate ceramic etc.], Z. Orthop. 115, (1977), 693–699) in order to make it possible for bone to penetrate as quickly as possible.

That aspect is a feature of many products corresponding to the prior art. However, macroporous products of that kind corresponding to the prior art have serious disadvantages, which shall be discussed below:

- one of the current methods for producing a macroporous structure consists of adding porosity-imparting agents, which are introduced, for example, in the form of foams or spherical plastics, which give rise to spherical pores on solidification of a hydraulically setting starting compound or on ceramic baking.

That porosity-imparting method has the disadvantage that the pores are predominantly closed. They are accordingly not available for penetration by budding-in bone and, in the end, result only in lowering of the strength of the implant region.

- A similar effect is produced by porosity-imparting methods carried out in many different ways by burning out irregularly shaped organic "spacer materials". In ceramics technology, sawdust, for example, is conventionally used. In that method and in numerous similar porosity-imparting media, irregularly distributed pore shapes and sizes are formed—which can be described as statistical porosity—which are used in ceramics technology for reducing the weight of the materials concerned and for improving thermal insulation. Statistical porosities of that kind are also used, based on those methods, in biomaterials according to the prior art. They are, however, completely unsuitable for the purpose, for the following reasons: Statistical porosities contain a wide spread of pore radius distribution, as well as, especially, numerous closed pores and pore tracks having "dead ends", which are unsuitable for homogeneous and complete penetration by bone.

- Building on that finding, a further kind of pore structure, obtained from biogenic products, is also currently in use. One such pore structure is so-called spongy bone, for example from cattle bone, which for the purpose of being used as implant material, is conditioned by more or less complete removal of protein constituents. Also used are the porous structures of corals and certain algae in order to obtain pore structures which, in view of their biogenic formation, are apparently optimal. Apart from the chemically questionable properties of such substances (for example, undefined chemical compositions and immunological problems in the case of cattle bone etc., as well as chemical activities that are entirely different to that of bone in the case of the use of algae and corals), there are also reasons of principle why such pore structures cannot be considered especially suitable. To begin with, it may first be stated that although the mentioned pore structures, as end products of a cybernetic modification process, have formed optimally modified systems in the original organisms in question, those systems no longer bear any relation to the biomechanical demands in the implant site. (In such a biomaterial, bone can necessarily only form in the open pore spaces, which in the original organism were holes or, in other words, were not biofunctional loading zones. At best, therefore, the "negative" of a functional bone structure can be formed.) Even disregarding such relatively "philosophical" reasons, the basic arguments against "statistical porosities" also argue against such structures: In the case of such biogenic pore structures, ingrowing bone structures are also impeded, for example, as a result of pores that are too small, or the osteons budding in are prevented, by numerous changes in direction, from achieving a biofunctional, lamellar orientation as quickly as possible, actually causing the formation of "woven bone", which grows in unordered fashion.

The invention accordingly relates to a resorbable bone replacement and bone formation material (augmentation material) based on porous β-tricalcium phosphate (β-TCP).

In the case of the formation material according to the invention, the macropores, seen in themselves, can contribute approximately 35% to the overall porosity (that is to say, microporosity+macroporosity) of the material. In spite of the high overall porosity of more than 50%, the strength of this implant material, compared to a statistical porosity of the same order of magnitude, is still sufficiently high for formed implant pieces still to be very readily handled. Without doubt, however, the strengths are so low here that functional strengths of the implant sites cannot be achieved without additional mechanical supporting devices, such as, for example, an external fixation or the known screw arrangements with plates etc. in many cases immediately after implantation. One of the crucial advantages of the formation material according to the invention is, however, that cross-linking of the implant structure with functionally oriented and spatially cross-linked bone structures takes place very rapidly so that, compared to other implant materials corresponding to the prior art, very rapid restoration of the functional roadability of the implant zotie is achieved. Consequently, the naturally low strength of calcium phosphate materials is compensated solely by the macroporous structure according to the invention. Even during the penetration phase of such structures, the osteons that bud in, which are already matched in their functional orientation to the loading situation, quickly supply the entire implant region with vessels and, consequently, ensure rapid resorption of the formation material according to the invention, with—simultaneously—a biofunctionally loadable state being very quickly achieved. The bone replacement and formation material according to the invention meets the general requirement for restoration of the implant site as quickly as possible solely by means of the described features with respect to phase purity microporosity and function-matched macroporosity in ideal manner. Those positive factors can be further enhanced by combining the implant materials according to the invention with growth-promoting constituents of the patient's blood, the so-called platelet rich plasma or so-called bone morphogenic proteins. That can be accomplished, for example, by soaking the micro- and macro-porous spaces of the implant materials, immediately before the operation, with preparations, in liquid form, of the growth-promoting media.

Further aspects of the solution to the technical problems and advantages of the bone replacement and formation material according to the invention are set out hereinbelow.

The invention further relates to a formation material characterised in that the chemical and crystalline purity, the fabric structure, the microporosity and the macroporosity of the augmentation material make possible rapid, foreign-body-reaction-free, biochemically orientated integration and resorption in bone.

Furthermore, the formation material according to the invention can be characterised in that at least 99.5% of the material consists of pure β-tricalcium phosphate (β-TCP).

Furthermore, the formation material according to the invention can be produced by baking β-tricalcium phosphate (β-TCP) at least twice and especially at least three times and preventing the formation of thermodynamically stable adjacent phases of β-TCP.

Furthermore, the formation material according to the invention can be produced by
(i) baking a phosphate powder of a chemical composition the residue on baking of which yields theoretically chemically pure tricalcium phosphate as a sintered-together presynthesis product, and powdering that presynthesis product,
(ii) optionally baking the powdered presynthesis product together with phosphate powder according to step (i) and powdering the material obtained and optionally repeating step (ii) once or more than once,
(iii) compressing the powdered product obtained in step (i) or step (ii) together with phosphate powder according to step (i) to form blanks and subjecting the blanks formed to final ceramic baking and
(iv) providing the compressed or baked blanks with tubular pores.

Furthermore, the formation material according to the invention can be produced by
(i) starting from a presynthesis product obtainable by baking a phosphate powder of a chemical composition the residue on baking of which yields theoretically chemically pure tricalcium phosphate as a sintered-together presynthesis product, and powdering that presynthesis product,
(ii) optionally baking the powdered presynthesis product together with phosphate powder according to step (i) and powdering the material obtained and optionally repeating step (ii) once or more than once,
(iii) compressing the powdered product obtained in step (i) or step (ii) together with phosphate powder according to step (i) to form blanks and subjecting the blanks formed to final ceramic baking and
(iv) providing the compressed or baked blanks with tubular pores.

Furthermore, the formation material according to the invention can be obtainable by baking at a temperature below 1200° C. in the β-tricalcium phosphate (β-TCP) phase region.

Furthermore, the formation material according to the invention can be obtainable by using in step (ii) and/or step (iii) from 1 to 50% by weight, especially from 1 to 25% by weight, phosphate powder (based on the total weight of phosphate powder and already baked material).

Furthermore, the formation material according to the invention can be characterised in that the sintered structure has a uniform, interconnected microporosity with pore widths in the region of from 2 to 15 μm and especially from 4 to 10 μm and/or the matrix of the augmentation material is tightly sintered to microporosity, especially with microparticles that are loosely incorporated in the sintered structure and/or phagocytosable, having a diameter of max. 15 μm, being absent.

Very advantageous cellular reactions are found if the bone replacement material has the structural parameters according to the invention: As a result of the production route, which shall be discussed hereinbelow, the material according to the invention is distinguished by an open, interconnecting microporosity having pore widths of from 2 to 15 μm. The ceramic matrix itself constitutes a network of tight structural elements firmly sintered to one another, in which loosely incorporated sub-particles, which could be dissolved out by cell activities, are absent.

Furthermore, the formation material according to the invention can be characterised by a microporosity of 20% by volume or more, preferably from 20 to 40% by volume, and especially 30% by volume or more, of the overall porosity (consisting of micro- and macro-porosity).

Also characteristic of the micro-structure according to the invention are the rounded surfaces of the fabric-forming structural elements (cf. FIG. 1), which relate especially advantageously to the living cells in the implant site, because mechanically induced irritation of the site tissue is largely avoided as a result. Those rounded fabric elements also cause stress and strain in the materials science sense to be minimised so that the materials according to the invention have optimum mechanical strength despite their comparatively high microporosity of more than 30% by volume.

Furthermore, the formation material according to the invention can be obtainable by providing the compressed, blank with tubular pores with the aid of a compression mould of optionally more than one part.

Furthermore, the formation material according to the invention can be obtainable by providing the baked blank with tubular pores by means of milling or drilling.

Furthermore, the formation material according to the invention can be characterised in that the formation material is in block form, with 2- or 3-dimensionally oriented macroscopic tubular pores passing through each block, which are in each case arranged perpendicular to the block surface or to an imaginary plane laid through the block or against the block and form an interconnecting system of tubular pores.

Furthermore, the formation material according to the invention can be characterised in that a block intended for implantation, together with its tubular pores, can be so oriented for implantation or on processing prior to implantation that at least one direction of orientation of the tubular pores corresponds to a biomechanically or biofunctionally intended direction of growth.

Furthermore, the formation material according to the invention can be characterised by tubular pores that have radii in the region of from 100 to 2000 μm and especially from 500 to 2000 μm.

In contrast to the prior art, the bone replacement and formation material according to the invention is provided with a very regularly oriented tubular porosity which, with radii of preferably from 500 to 2000 μm, has optimum size characteristics for the budding-in of osteons. Such pores of parallel arrangement pass through the materials according to the invention in at least two, in certain applications even three, tubular systems arranged perpendicular to one another. For optimum matching, to the functional task, one of the tube orientations on implantation should be in accordance with the main direction of growth of the adjacent host bone. Because the pore systems arranged perpendicular to one another in the implant materials according to the invention interconnect in all planes, the bone structures that bud in cross-link very quickly to form a well vascularised spatial network of load-bearing bone structures. As a result, the bone formation material according to the invention constitutes, in the truest sense of the term, an optimum guide rail system.

That accords with studies by Klawitter et al. (Klawitter, J. J. et al.: An Evaluation of Bone Growth into Porous High Density PE. J.Biomed.Res. 10:311, 1976), according to which the smallest functional building elements of bone, the osteons, which are tube-like structures having complete supply organs for maintaining vital functions, can only grow into pore tracks that have a pore width of at least 100 µm. Smaller pore systems do not permit biofunctional penetration by living bone. From that it follows that biomaterials having statistical pore systems, for example those corresponding to the current prior art, cannot be a satisfactory solution.

Furthermore, the formation material according to the invention can be characterised in that the formation material, present in block form, is penetrated by the tubular pores spaced apart at a defined spacing with respect to one another, especially at a spacing that corresponds to a wall thickness of not more than from 1500 to 4000 µm and especially from 2000 to 3000 µm.

According to further investigations upon which the invention is based, the critical material thicknesses in the case of monolithic material structures having solely microporosity are above 3–4 mm. If the wall thickness is lower, the body fluids can be exchanged with the surrounding living tissue by means of diffusive processes so that necrotic processes do not take place.

The requirement arrived at above in the section "Microporosity" for wall thicknesses of not more than from 3 to 4 mm is met in the defined macroporous material according to the invention by means of the fact that the tubular pores are set so closely together that the material thicknesses are at no point greater than about 3 mm.

Furthermore, the formation material according to the invention can be characterised by an overall porosity (consisting of micro- and macro-porosity) of more than 50% by volume.

Furthermore, the formation material according to the invention can be characterised by a macroporosity of from 25 to 50% by volume, and especially from 30 to 40% by volume, of the overall porosity (consisting of micro- and macro-porosity).

Furthermore, the formation material according to the invention can be characterised in that the block form is a simple geometric shape, especially that of a cube, cuboid, taper, cone or disc.

Furthermore, the formation material according to the invention can be characterised in that it is a semi-finished product, especially for subsequent mechanical processing, preferably for individual adaptation in the case of a bone defect in mouth or jaw medicine, orthopaedic surgery or trauma surgery.

Furthermore, the formation material according to the invention can be characterised in that the material is compressed, especially baked or sintered, only to a degree such that it can be processed using tools available to the practitioner, especially using a rasp, file, scalpel or a dentist's instrument.

Furthermore, the formation material according to the invention can be characterised in that it has been brought into the form of an individual prosthesis with the aid of a medical CAD/CAM method.

The invention is illustrated in further detail hereinafter by means of figures and implementation examples, wherein:

FIG. 4a is a graph of intensity (CPS) versus 2 Theta (degrees) of an X-ray recording of an exemplary material after a first (CPS) sinter bake.

FIG. 4b is a graph of intensity (CPS) versus 2 Theta (degrees) of the material shown in FiE. 4a after further processing and a second sinter bake;

FIG. 5a is a graph of intensity (CPS) versus 2 Theta (degrees) of an X-ray of a different material batch after a first baking; and FIG. 5b is a graph of intensity (CPS) versus 2 Theta (degrees) of the material shown in FIG. 5a after further processing and a second sinter bake.

IMPLEMENTATION EXAMPLES

1. According to an advantageous embodiment, the ceramic implant material according to the invention can be synthesised from the two inorganic materials calcium hydrogen phosphate and calcium carbonate from stoichiometric mixtures by sintering according to the formula

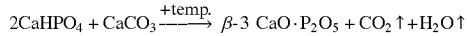

$$2CaHPO_4 + CaCO_3 \xrightarrow{+temp.} \beta\text{-}3\ CaO\cdot P_2O_5 + CO_2 \uparrow + H_2O \uparrow$$

The synthesis is carried out at temperatures below 1200° C. in the β-TCP phase region. In order to avoid the formation of undesirable subsidiary phases such as that of β-TCP, of amorphous phases and of hydroxyapatite, rectification of the material is carried out by sintering several times in the above-mentioned temperature range.

2. Forming of the implant material according to the invention is advantageously carried out by compressing the phase-pure TCP powder to form long cylindrical blanks, baking these at T<1200° C. and bringing the blanks obtained in that matter into the desired form by means of chip-removing methods (milling, turning and drilling).

Figure 1:
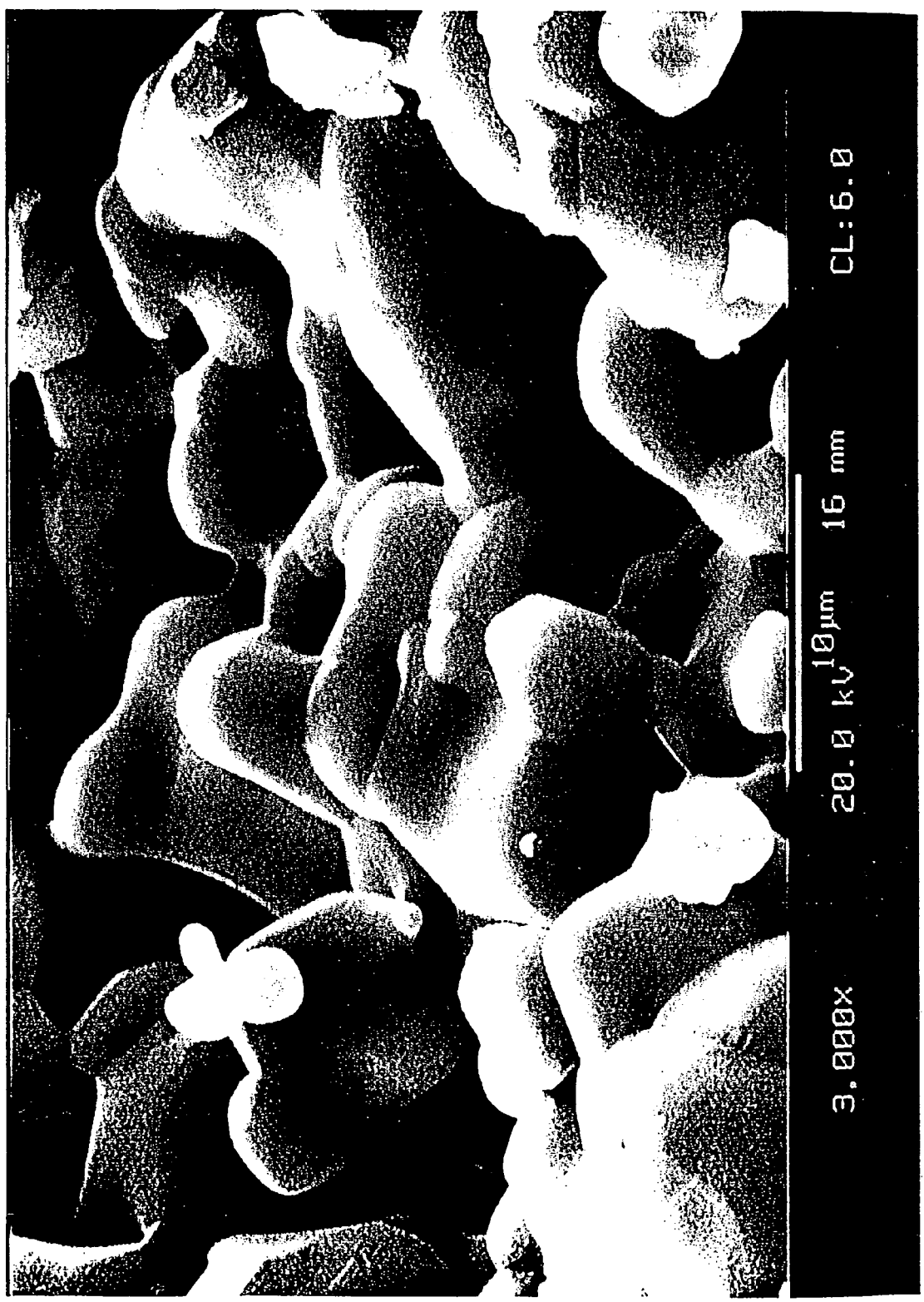
FIG. 1 shows the micro-structure of an augmentation material according to the invention.
Figure 2:
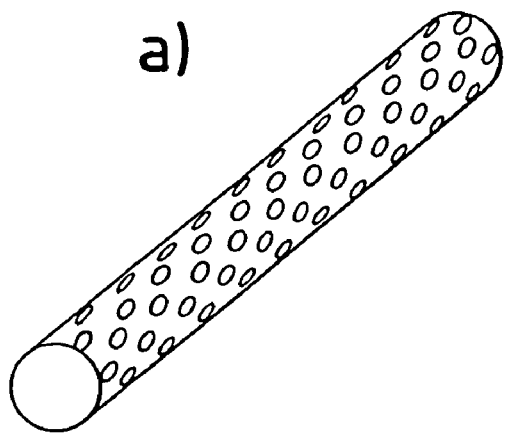
FIGS. 2a to 2e show examples of augmentation articles according to the invention in the form of semi-finished products.
Figure 2:
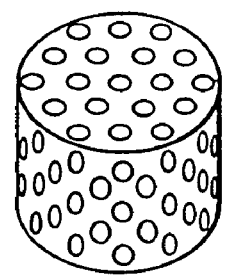
Figure 2:
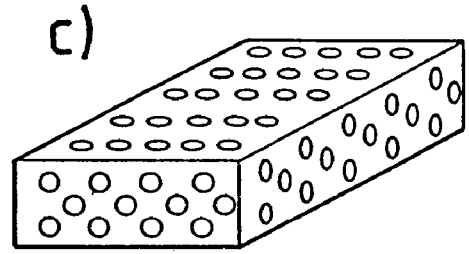
Figure 2:
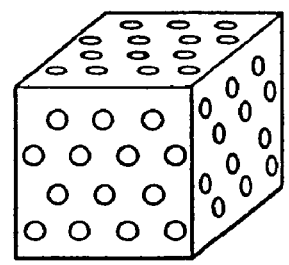
Figure 2:
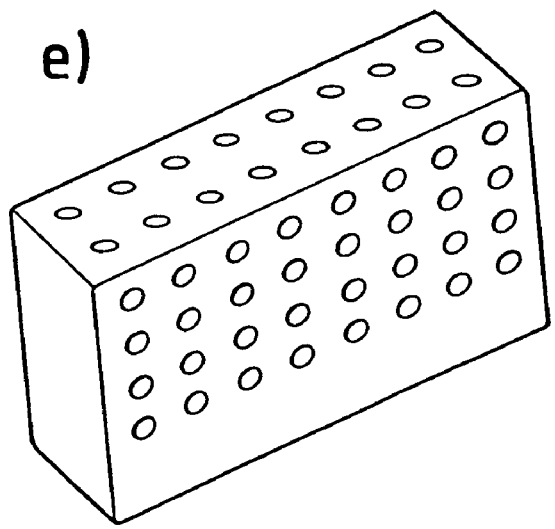

3. Manipulable implants can be produced, according to an advantageous embodiment, from the bone replacement material according to the invention, in the form of rod-shaped cylindrical, cuboidal or cube-shaped and other semi-finished products which can be brought into the desired shaped using suitable tools (files, rasps, saws etc.) (cf. FIG. 2). Those semi-finished products can be produced by customary compressing techniques from powders but also by pouring techniques of the kind that is customary in ceramics. The tubular porosity according to the invention is produced by drilling and milling after ceramic baking of those shaped articles.

Figure 3:
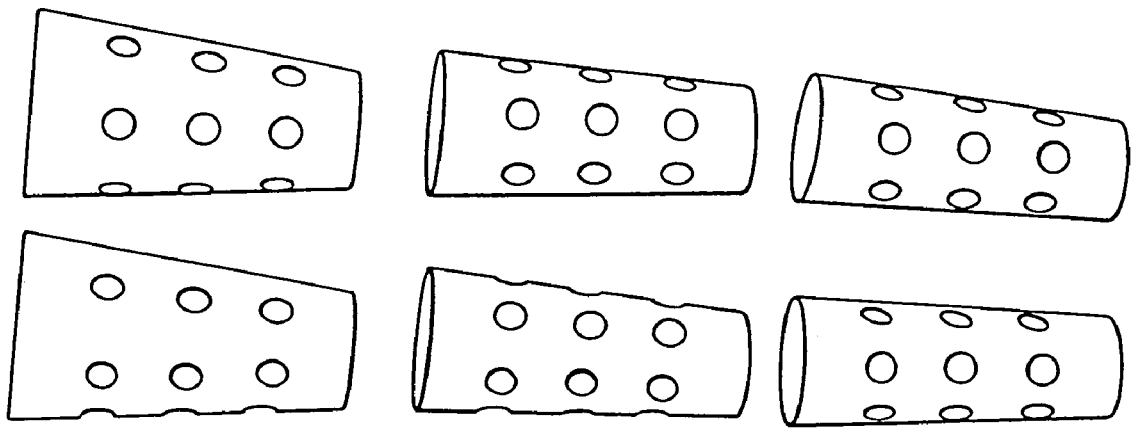
FIG. 3a shows an alveolar augmentation article according to the invention.
FIG. 3b shows an augmentation article according to the invention for a trephination closure.
FIG. 3c shows an augmentation article according to the invention in the form of a sinus lift.
Figure 3:
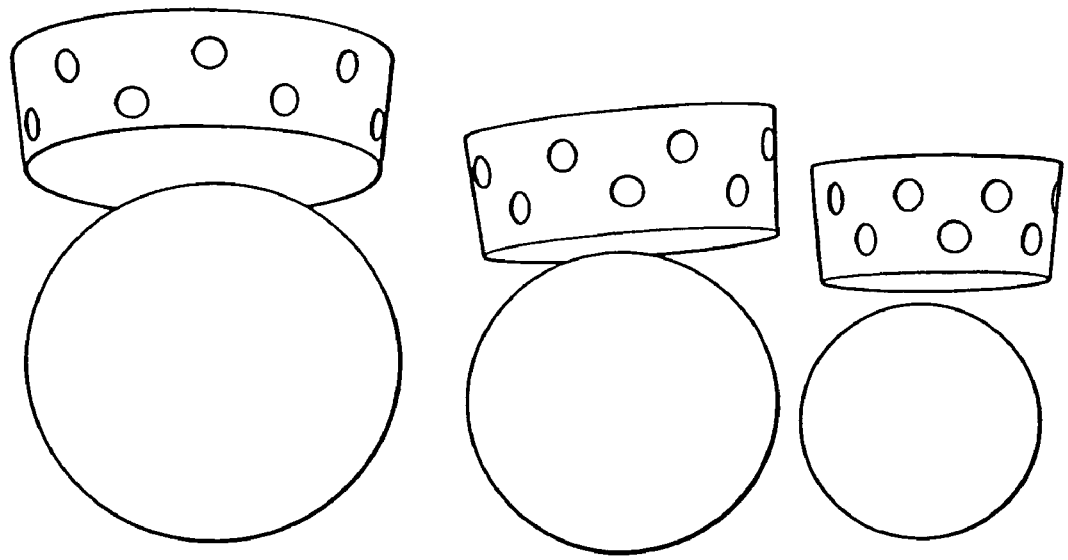
Figure 3C:
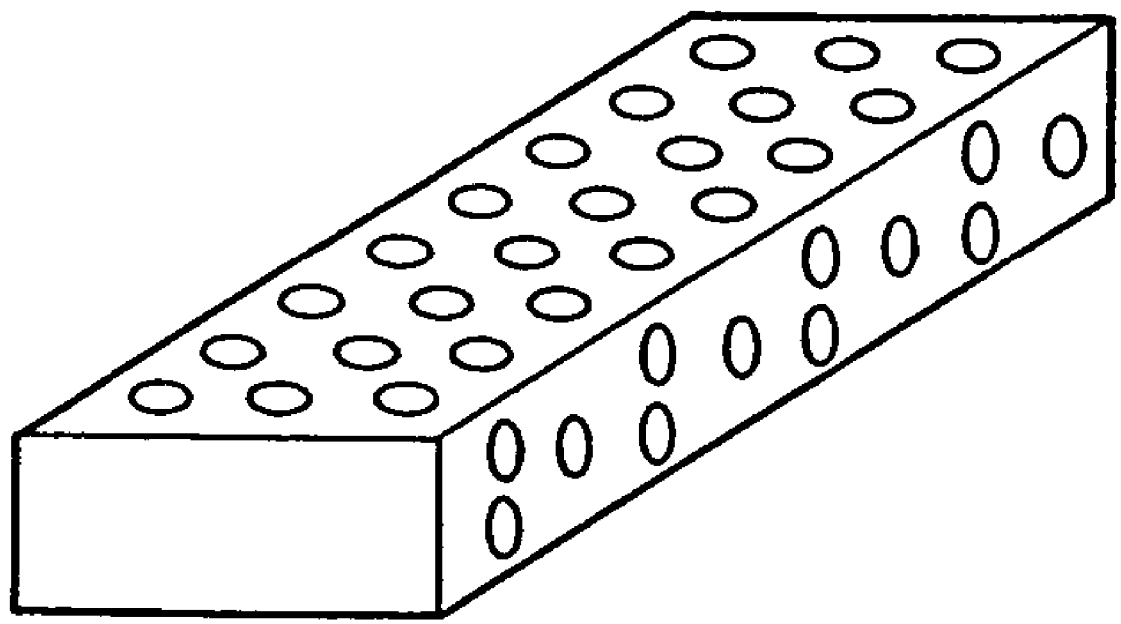

4. Particular implants made from the material according to the invention, which are employed in specific fields of use, can be produced in large numbers in standardised size gradations from blanks by, for example, chip-removing methods. A number of advantageous embodiments are shown in FIG. 3a–c. For example, FIG. 3a shows a so-called alveolar augmentation article for filling an alveolus after extraction of a tooth; FIG. 3b shows a conical disc which serves for closure of a trephination opening in the cranium; FIG. 3c shows an advantageous embodiment of a flat augmentation article for filling out or raising an atrophied jaw ridge, a so-called sinus lift.

5. 2 mol of calcium hydrogen phosphate and 1 mol of calcium carbonate in powder form were mixed, compressed to make a formed element, transferred to a ceramic crucible and sintered for 24 hours at 1100° C. The sintered element was broken up and ground; 1% of an unreacted powder mixture of the formulation given above was added thereto and intimately mixed therewith. The mixture was then compressed to make a formed element and again sintered for 24 hours at 1100° C. After cooling, the sintered element obtained was mechanically processed and brought into a form according to FIG. 2e. The formed piece was finally baked again for 24 hours at 950° C.

6. Experimental Results

The successful development step for achieving phase-pure β-TCP ceramics is documented by two X-ray recordings (FIGS. 4a, 4b). FIG. 4a shows the material after the first sinter bake. Still clearly discernible is a residual reflection of hydroxyapatite (arrow). After a first sinter bake, the batch was broken up again, homogenised and compacted again. No unreacted starting material was added to the material. The X-ray powder diffraction diagram still shows a residual reflection of hydroxyapatite after that second sinter bake.

Using a second example, it may be demonstrated that the hydroxyapatite foreign phase is, surprisingly, no longer discernible as a result of the addition of unreacted starting material to a batch of β-TCP baked once. After the first sinter bake, the batch K 286 clearly shows a HA reflection at about 31.7°2θ. After again powdering the pre-synthesised material and mixing with unreacted phosphate powder, the resulting material was also subjected to a second sinter bake. In FIG. 5b, an HA reflection is no longer discernible.

It is accordingly possible here to demonstrate impressively that the formation of HA is completely suppressed as a result of dissolution thereof in the melt after unreacted material is added, with, at the same time, seed formation being facilitated by the β-TCP already present.

That which is claimed:

1. A bioresorbable bone augmentation, filler and/or replacement product, comprising:
   a bioresorbable porous crystalline shaped body of β-tricalcium phosphate with a substantial degree of phase purity comprising micro pores and macro pores, each macro pore having a substantially constant width over at least a major portion of a respective length thereof.

2. A product according to claim 1, wherein the shaped body has at least about 99.5% by weight phase pure β-tricalcium phosphate.

3. A product according to claim 1, wherein the shaped body consists essentially of sintered crystalline β-tricalcium phosphate that defines the micro pores and forms tubular macro pores.

4. A product according to claim 1, wherein the macropores are substantially tubular along respective lengths thereof, wherein the micropores are defined by a compressed sintered matrix of β-tricalcium phosphate particles, and wherein the micropores are interconnected and distributed to thereby provide an interconnecting matrix of micropores that interconnect the substantially tubular macropores.

5. A product according to claim 1, wherein the shaped body β-tricalcium phosphate is defined by particles of sintered β-tricalcium phosphate, and wherein at least a plurality of the macropores are substantially tubular and arranged in the shaped body so that at least one extends across the shaped body at a different angular orientation with respect to at least another one so that some of the tubular macropores cross through others and are open to an external surface of the shaped body to thereby form an open matrix of interconnecting macropores and micropores.

6. A product according to claim 1, wherein the micropores are interconnected and distributed about the shaped body.

7. A product according to claim 6, wherein the micropores are substantially uniformly distributed in at least two dimensions about the shaped body.

8. A product according to claim 7, wherein the micropores are defined by a sintered structure of β-tricalcium phosphate particles that provide micropore widths of less than about 20 μm.

9. A product according to claim 1, wherein the shaped body is configured with sintered β-tricalcium phosphate particles having mechanical stability and/or structure sufficient to allow a clinician to customize the shaped body in situ prior to implantation and/or to inhibit undesirable phagocytosable activity in position in vivo.

10. A product according to claim 1, wherein the shaped body comprises a network of particles of β-tricalcium phosphate sintered together forming an interconnected micropore matrix with adjacent particles firmly attached at abutting contact surfaces to thereby inhibit premature disintegration into loose microparticles.

11. A product according to claim 1, wherein the shaped body has an overall porosity of at least about 20% by volume.

12. A product according to claim 1, wherein the shaped body has an overall porosity of at least about 50% by volume.

13. A product according to claim 1, wherein the product is configured as a semi-finished manipulable shaped body with sufficient rigidity and/or mechanical strength to thereby allow further exterior manipulation prior to implantation.

14. A product according to claim 1, wherein the shaped body is configured with sufficient structural rigidity and/or mechanical strength to allow a clinician to alter its configuration to a desired shape thereby retaining a desired configuration without the shaped body breaking apart and/or disintegrating into granular or powder form.

15. A product according to claim 1, wherein the shaped body consists essentially of a compressed sintered matrix structure of β-tricalcium phosphate particles that define interconnected micropores.

16. A product according to claim 1, wherein the shaped body comprises about 20% or greater microporosity by volume.

17. A product according to claim 1, wherein the shaped body comprises about 25% or greater macroporosity by volume, and wherein the macropores are substantially tubular macropores.

18. A product according to claim 1, wherein the macropores comprise a plurality of substantially tubular macropores, and wherein respective macropores have a generally constant radius over a respective length thereof.

19. A product according to claim 18, wherein the tubular macropores are non-uniformly distributed over the shaped body, and wherein the micropores interconnect the macropores.

20. A product according to claim 18, wherein the tubular macropores are generally uniformly distributed over a length and/or width of the shaped body, and wherein the micropores interconnect the macropores.

21. A product according to claim 1, wherein the macropores are substantially tubular, and wherein a plurality of the tubular macropores are configured to extend in a generally common direction through the shaped body so that, in position, the plurality of tubular macropores substantially are oriented to align with a primary direction of growth of adjacent host bone at an implant site.

22. A product according to claim 1, wherein the macropores are elongate and arranged so that a first plurality of the elongate macropores extend in a first direction through the shaped body and a second plurality of elongate macropores extend in a second direction through the shaped body, and wherein at least one of the first and at least one of the second plurality of elongate macropores are configured to intersect in the shaped body and provide an interconnecting macropore and micropore system.

23. A product according to claim 1, wherein the macropores are substantially tubular with a first plurality of the tubular macropores extending in a generally common predetermined first direction, the first direction selected to align with a target direction of primary growth in vivo to thereby provide a guide rail system that promotes bone growth.

24. A product according to claim 23, wherein the first plurality of tubular macropores are generally in parallel arrangement.

25. A product according to claim 23, wherein the tubular macropores comprise a second plurality of tubular macropores extending in a generally common predetermined second direction that is different from the first direction, so that at least some of the first plurality and second plurality of tubular macropores cross through each other to thereby define interconnecting macroporosity.

26. A product according to claim 25, wherein the first direction is substantially perpendicular to the second direction.

27. A product according to claim 1, wherein the macropores have a generally constant predetermined tubular pore size along at least a major portion of a length of respective pores to thereby promote rapid angiogenesis in vivo.

28. A product according to claim 1, wherein the shaped body is generally cylindrical, wherein the macropores are substantially tubular, and wherein a plurality of the macropores are generally circumferentially spaced apart about the shaped body.

29. A product according to claim 1, wherein the macropores comprise a first plurality of substantially tubular macropores, each of the tubular macropores having a respective center axis, and wherein the center axes of the first plurality of tubular macropores are generally parallel.

30. A product according to claim 27, wherein the macropores are substantially tubular, wherein sintered β-tricalcium phosphate particles define the micropores, and wherein the micropores and macropores are configured to define an interconnecting pore system.

31. A product according to claim 27, wherein the macropores are substantially tubular with radii of between about 100–2000 μm.

32. A product according to claim 31, wherein the macropores have radii of between about 500–2000 μm.

33. A product according to claim 1, wherein the shaped body consists essentially of attached sintered β-tricalcium phosphate particles that define an interconnected micropore matrix, and wherein the matrix of sintered particles comprises rounded particle surfaces thereby inhibiting irritation of site tissue in vivo.

34. A product according to claim 1, wherein the shaped body is devoid of thermodynamically stable adjacent phases of β-tricalcium phosphate.

35. A product according to claim 1, wherein the macropores are substantially tubular with a generally constant radius along respective lengths thereof, wherein the shaped body comprises compressed sintered β-tricalcium phosphate particles that define an interconnected micropore matrix with irregularly sized micropores distributed through the shaped body to interconnect the tubular macropores.

36. A product according to claim 1, wherein the macropores are substantially tubular with a respective center axis, and wherein at least a portion of the generally tubular macropores are arranged so that their respective center axis is generally parallel to and generally regularly spaced apart from other macropores.

37. A product according to claim 1, wherein the shaped body includes macropores that are spaced apart from each other a distance to provide a wall thickness therebetween of less than about 4000 μm.

38. A product according to claim 1, wherein the macropores in the shaped body are substantially tubular and are configured so that the largest distance between adjacent macropores is less than about 4000 μm.

39. A product according to claim 1, wherein, in at least one predetermined direction, the macropores are generally uniformly spaced apart and extend substantially straight through the shaped body.

40. A product according to claim 38, wherein the macropores are spaced apart between about 1500–2000 μm.

41. A product according to claim 1, wherein the macropores are substantially tubular pores that are arranged on the shaped body so that the material thickness between adjacent generally tubular pores is about 3 mm or less.

42. A product according to claim 1, wherein the porosity is configured in the shaped body with pore systems arranged substantially perpendicular to each other with open pore tracks and a generally uniformly distributed microporosity network.

43. A product according to claim 37, wherein macropores are substantially tubular and are generally uniformly arranged so that the tubular pores extend through the shaped body in three dimensions.

44. A product according to claim 39, wherein the shaped body has a pore distribution of at least about 20% macroporosity by volume and at least about 20% microporosity by volume.

45. A product according to claim 1, wherein the shaped body is configured with sintered β-tricalcium phosphate particles defining the micropores, and wherein the sintered β-tricalcium phosphate particles are devoid of particles sized at about 15 μm or less to thereby inhibit phagocytosable activity in position in vivo.

46. A bioresorbable bone augmentation, filler and/or replacement product, comprising:

a porous bioresorbable shaped body consisting essentially of sintered β-tricalcium phosphate having macro and micro pores, with the macropores comprising substantially tubular macropores that define open cavities extending through the body, wherein a first plurality of the macropores are oriented to extend through the shaped body in a generally common first direction, wherein, in position, the first plurality of tubular-macropores of the shaped body are generally aligned with the primary direction of growth of adjacent host bone in an implant zone to thereby provide a guide rail system that thereby promotes restoration of the functional loadability of the implant zone and/or resorption of formation material.

47. A product according to claim 46, wherein the shaped body further comprises a second plurality of substantially tubular macropores extending therethrough in generally parallel alignment, the second set of tubular macropores being arranged to extend in a different direction than that of the first plurality of macropores, and wherein at least some of the first and second plurality of macropores are configured to intersect with each other and/or the micropores and provide an interconnecting system of pores.

48. A product according to claim 47, wherein the shaped body further comprises a third plurality of substantially tubular macropores extending therethrough, the third plurality of macropores arranged to extend in a third direction different than the first and second directions and intersect with the first and second plurality of macropores to thereby provide a three-dimensional interconnecting system of tubular macropores.

49. A product according to claim 46, wherein the micropores are defined by a compressed sintered matrix of β-tricalcium phosphate particles.

50. A product according to claim 49, wherein the sintered matrix is substantially devoid of loosely incorporated microparticles having a diameter of about 15 $\mu$m or less.

51. A product according to claim 46, wherein the macropores in the shaped body are configured so that the largest distance between adjacent macropores is less than about 4000 $\mu$m.

52. A product according to claim 46, wherein the shaped body has an overall porosity of about 50% or greater.

53. A product according to claim 46, wherein the shaped body substantially consists essentially of crystalline pure β-tricalcium phosphate.

54. A product according to claim 53, wherein the β-tricalcium phosphate is about 99.5% or greater in phase purity.

55. A shaped body of resorbable bone augmentation material consisting essentially of a sintered matrix of beta-tricalcium phosphate that defines interconnected micropores, wherein the shaped body further comprises macropores having a substantially constant width along at least a major portion of their length and extending in at least one selected direction through the shaped body.

56. A shaped body according to claim 55, wherein the β-tricalcium phosphate is substantially crystalline having substantial phase purity, and wherein the macropores and micropores interconnect.

57. A shaped body according to claim 55, wherein the shaped body is by weight at least about 99.5% phase pure β-tricalcium phosphate.

58. A shaped body according to claim 55, wherein the shaped body comprises at least about 20% microporosity by volume.

59. A shaped body according to claim 55, wherein the shaped body comprises about 25% or greater macroporosity by volume.

60. A shaped body according to claim 56, wherein the shaped body has an overall porosity of about 50% or greater.

61. A shaped body according to claim 55, wherein the macropores are substantially tubular with at least a portion of the tubular macropores arranged to be substantially parallel to each other, each tubular macropore having a substantially constant width over a respective macropore length.

62. A shaped body of resorbable bone augmentation material consisting essentially of sintered crystalline beta-tricalcium phosphate having a substantial degree of phase purity by weight and comprising interconnected micro and macro pores, wherein the micro pores and macro pores are non-spherical.

63. A shaped body according to claim 62, wherein the shaped body has an overall porosity of about 50% or greater, and wherein the macropores have an average width of about 20 $\mu$m or less.

64. A shaped body according to claim 62, wherein the macropores are configured as apertures with substantially uniform diameters along at least a major portion of a length thereof that extend through the shaped body in at least one direction.

65. A shaped body according to claim 64, wherein the macropore apertures are substantially tubular.

66. A shaped body according to claim 65, wherein at least a first plurality of the tubular apertures are arranged to be generally parallel to each other, each having a generally constant width over at least a major portion of a respective length thereof.

67. A shaped body according to claim 66, wherein the first plurality of generally parallel tubular apertures are configured so that, in position, the first plurality of generally parallel tubular apertures are oriented to substantially align with a primary direction of growth in host bone in a target implant site.

68. A shaped body according to claim 67, further comprising a second plurality of macropores having apertures with a substantially constant width over at least a major portion of a length thereof that extend through the shaped body in a different direction from the first plurality of apertures so that at least one of the second plurality of macropores intersects at least some of the first plurality of macropores to thereby provide an interconnecting system of macropores and micropores.

69. A shaped body according to claim 65, wherein the shaped body consists essentially of a compressed sintered matrix structure of beta-tricalcium phosphate particles that define the interconnected micropores, and wherein the macropores are substantially tubular and arranged in the body so that at least some extend therethrough in different non-parallel orientations with respect to some of the others.

70. A shaped body according to claim 62, wherein the shaped body comprises about 20% or greater microporosity by volume.

71. A shaped body according to claim 69, wherein the shaped body comprises about 25% or greater macroporosity by volume.

72. A shaped body according to claim 62, wherein the shaped body comprises substantially tubular macropores, each tubular macropore having a generally constant predetermined tubular pore width along a length of a respective macropore that is in fluid communication with a micropore matrix to thereby promote rapid angiogenesis in vivo.

73. A three-dimensional shaped body of resorbable bone augmentation material consisting essentially of a compressed body of sintered beta-tricalcium phosphate defining an interconnected matrix of micropores and a plurality of substantially tubular macropores in fluid communication therewith.

74. A shaped body according to claim 73, wherein the micropores are non-spherical and provide a microporosity that is at least about 20% by volume of the overall porosity.

75. A shaped body according to claim 73, wherein the macropores define a macroporosity that is at least about 25% by volume of the overall porosity.

76. A shaped body according to claim 73, wherein the substantially tubular macropores arranged so that a plurality extend through the shaped body in at least one different angular orientation with respect to others so that at least one macropore crosses through another, and wherein at least a first plurality of the tubular macropores are generally parallel to each other and, in position, are oriented to substantially align with a primary direction of growth in host bone in a target implant site.

77. A shaped body according to claim 73, wherein the tubular macropores comprise macropores that are arranged to extend through the shaped body to be generally parallel to each other and spaced apart a distance sufficient so that the material thickness therebetween is equal to or less than about 3 mm.

78. A shaped body according to claim 77, wherein the shaped body has a porosity of at least about 30% by volume.

79. A shaped body according to claim 77, wherein the shaped body has an overall porosity of about 50% or greater.

80. A shaped body according to claim 73, wherein the compressed body of sintered beta-tricalcium phosphate is configured with sintered beta-tricalcium phosphate particles having diameters greater than about 15 $\mu$m that define the interconnected matrix of micropores.

81. A resorbable bone augmentation shaped body $\beta$-tricalcium phosphate having substantially tubular macropores and an interconnected sintered matrix configuration of micropores with adjacent $\beta$-tricalcium phosphate particles being firmly sintered together with sufficient abutting contact surfaces therebetween to define the micropore structure and inhibit premature disintegration into loose microparticles in vivo.

82. A shaped body according to claim 81, wherein the shaped body has an overall porosity that is at least about 50% by volume.

83. A shaped body according to claim 82, wherein the shaped body has microporosity of about 20% by volume or greater, and wherein the micropores are nonspherical.

84. A shaped body according to claim 82, wherein the shaped body has macroporosity of about 25% by volume or great, with macropore radii between about 100–2000 $\mu$m.

85. A shaped body according to claim 82, wherein the micropores of the sintered matrix have cross-sectional widths that are about 20 $\mu$m or less.

* * * * *

UNITED STATES PATENT AND TRADEMARK OFFICE
CERTIFICATE OF CORRECTION

| | | |
|---|---|---|
| PATENT NO. | : 7,012,034 B2 | Page 1 of 1 |
| APPLICATION NO. | : 10/930965 | |
| DATED | : March 14, 2006 | |
| INVENTOR(S) | : Heide et al. | |

It is certified that error appears in the above-identified patent and that said Letters Patent is hereby corrected as shown below:

Column 8,
Line 25 should read -- (degrees) of the material shown in FIG 4a after further --

Column 9,
Line 56 should read -- a bioresorbable porous crystalline shaped body consisting essentially of sintered β-tri- --

Column 16,
Line 8 should read -- 81. A resorbable bone augmentation shaped body consisting essentially of sintered β-tri- --

Signed and Sealed this

Twelfth Day of September, 2006

JON W. DUDAS
*Director of the United States Patent and Trademark Office*